United States Patent
Brunner

(10) Patent No.: US 6,682,514 B1
(45) Date of Patent: Jan. 27, 2004

(54) EFFICIENT ZONED ELASTIC LAMINATE

(75) Inventor: Michael Scott Brunner, Roswell, GA (US)

(73) Assignee: Kimberly-Clark Worldwide Inc., Neenah, WI (US)

(*) Notice: Subject to any disclaimer, the term of this patent is extended or adjusted under 35 U.S.C. 154(b) by 0 days.

(21) Appl. No.: 09/346,399

(22) Filed: Jun. 30, 1999

(51) Int. Cl.$^7$ .............................................. A61F 13/15
(52) U.S. Cl. ........................ 604/385.24; 604/385.25; 604/385.26; 604/385.27
(58) Field of Search ................... 604/385.25, 385.24, 604/385.26, 385.27, 385.3, 394, 396; 57/200; 428/220, 221, 343, 157, 170, 300.4, 171, 172; 442/328, 329, 415

(56) References Cited

U.S. PATENT DOCUMENTS

| | | | |
|---|---|---|---|
| 3,497,415 A | 2/1970 | Adachi | 161/76 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 3,949,128 A | 4/1976 | Ostermeier | 428/152 |
| 4,205,679 A | 6/1980 | Repke et al. | 128/287 |
| 4,209,563 A | 6/1980 | Sisson | 428/288 |
| 4,296,163 A | 10/1981 | Emi et al. | 428/212 |
| 4,300,562 A | 11/1981 | Pieniak | 128/287 |
| 4,340,563 A | 7/1982 | Appel et al. | 264/518 |
| 4,366,814 A | 1/1983 | Riedel | 128/156 |
| 4,443,513 A | 4/1984 | Meitner et al. | 422/195 |
| 4,507,163 A | 3/1985 | Menard | 156/164 |
| 4,525,407 A | 6/1985 | Ness | 428/138 |
| 4,606,964 A | 8/1986 | Wideman | 428/152 |
| 4,652,487 A | 3/1987 | Morman | 428/138 |
| 4,657,802 A | 4/1987 | Morman | 428/152 |
| 4,663,220 A | 5/1987 | Wisneski et al. | 428/221 |
| 4,677,695 A | 7/1987 | Van Gompel et al. | 2/79 |
| 4,701,171 A | 10/1987 | Boland et al. | 604/385 A |

(List continued on next page.)

FOREIGN PATENT DOCUMENTS

| | | | |
|---|---|---|---|
| EP | 552 340 | 7/1993 | A61F/13/15 |
| EP | 552 345 | 7/1993 | A61F/13/15 |
| EP | 582 569 | 2/1994 | B32B/5/26 |
| EP | 602 613 | 6/1994 | D04H/1/56 |
| EP | 603 497 | 6/1994 | D04H/13/00 |
| EP | 604 731 | 7/1994 | B32B/31/00 |
| EP | 646 062 | 4/1995 | B32B/25/08 |
| EP | 662 811 | 7/1995 | A61F/13/15 |
| EP | 713 546 | 5/1996 | D04H/13/00 |
| EP | 788 874 | 8/1997 | B32B/5/24 |
| EP | 803 602 | 10/1997 | D04H/3/16 |
| EP | 806 196 | 11/1997 | A61F/13/15 |
| EP | 820 747 | 1/1998 | A61F/13/15 |
| FR | 2 716 085 | 8/1995 | A41F/19/00 |
| FR | 2 730 138 | 8/1996 | A41D/13/02 |
| GB | 2 262 035 | 6/1993 | A41F/09/02 |
| GB | 2 291 783 A | 2/1996 | A61F/13/15 |
| WO | WO 97/48357 | 12/1997 | A61F/13/15 |
| WO | 99/33427 | 7/1999 | A61F/13/15 |

OTHER PUBLICATIONS

U.S. application Ser. No. 09/267,412, filed Mar. 12, 1999, entitled "Segmented Conformable Breathable Film".

*Primary Examiner*—Weilun Lo
*Assistant Examiner*—Jacqueline F Stephens
(74) *Attorney, Agent, or Firm*—Pauley Petersen & Erickson

(57) ABSTRACT

A garment is provided with an elastomeric element having first and second elastic segments made of different elastomeric polymers and connected in series. The first elastic segment can be made from a relatively higher performance, more expensive polymer. The second elastic segment can be made from a relatively less expensive elastic polymer having moderate performance characteristics. The hybrid elastic band provides durable high elastic performance in regions of the garment where these properties are needed, while minimizing the total cost of the band.

26 Claims, 2 Drawing Sheets

U.S. PATENT DOCUMENTS

| | | | |
|---|---|---|---|
| 4,707,398 A | 11/1987 | Boggs | 428/224 |
| 4,720,415 A | 1/1988 | Vander Wielen et al. | 428/152 |
| 4,781,966 A | 11/1988 | Taylor | 428/152 |
| 4,863,779 A | 9/1989 | Daponte | 428/152 |
| 4,935,287 A | 6/1990 | Johnson et al. | 428/198 |
| 4,965,122 A | 10/1990 | Morman | 428/225 |
| 4,981,747 A | 1/1991 | Morman | 428/198 |
| 5,032,122 A | 7/1991 | Noel et al. | 604/391 |
| 5,114,781 A | 5/1992 | Morman | 428/198 |
| 5,116,662 A | 5/1992 | Morman | 428/198 |
| 5,143,679 A | 9/1992 | Weber et al. | 264/288.8 |
| 5,156,793 A | 10/1992 | Buell et al. | 264/288.8 |
| 5,167,897 A | 12/1992 | Weber et al. | 264/288.8 |
| 5,230,701 A | 7/1993 | Meyer et al. | 602/76 |
| 5,278,272 A * | 1/1994 | Lai et al. | 526/348.5 |
| 5,304,599 A | 4/1994 | Himes | 525/98 |
| 5,332,613 A | 7/1994 | Taylor et al. | 428/152 |
| 5,340,424 A | 8/1994 | Matsushita | 156/164 |
| 5,344,691 A | 9/1994 | Hanschen et al. | 428/152 |
| 5,382,461 A | 1/1995 | Wu | 428/86 |
| 5,393,599 A | 2/1995 | Quantrille et al. | 428/284 |
| 5,422,172 A | 6/1995 | Wu | 428/230 |
| 5,440,764 A | 8/1995 | Matsushita | 2/401 |
| 5,447,462 A | 9/1995 | Smith et al. | 450/122 |
| 5,451,450 A | 9/1995 | Erderly et al. | 428/220 |
| 5,460,861 A | 10/1995 | Vicik et al. | 428/34.9 |
| 5,468,428 A | 11/1995 | Hanschen et al. | 264/483 |
| 5,472,775 A * | 12/1995 | Obijeski et al. | 428/220 |
| 5,486,273 A | 1/1996 | Widlund et al. | 264/154 |
| 5,500,063 A | 3/1996 | Jessup | 156/85 |
| 5,503,908 A | 4/1996 | Faass | 428/198 |
| 5,518,801 A | 5/1996 | Chappell et al. | 428/152 |
| 5,529,830 A | 6/1996 | Dutta et al. | 428/176 |
| 5,540,976 A | 7/1996 | Shawver et al. | 428/198 |
| 5,545,158 A | 8/1996 | Jessup | 604/385.2 |
| 5,569,232 A | 10/1996 | Roe et al. | 604/385.2 |
| 5,592,690 A | 1/1997 | Wu | 2/67 |
| 5,614,297 A | 3/1997 | Velazquez | 428/218 |
| 5,634,216 A | 6/1997 | Wu | 2/239 |
| 5,650,214 A | 7/1997 | Anderson et al. | 428/152 |
| 5,675,842 A | 10/1997 | Schaefer | 2/237 |
| 5,681,645 A | 10/1997 | Strack et al. | 428/196 |
| 5,691,035 A | 11/1997 | Chappell et al. | 428/152 |
| 5,695,849 A | 12/1997 | Shawver et al. | 428/131 |
| 5,709,921 A | 1/1998 | Shawver | 428/152 |
| 5,733,822 A | 3/1998 | Gessner et al. | 442/35 |
| 5,769,838 A * | 6/1998 | Buell et al. | 604/396 |
| 5,789,065 A | 8/1998 | Haffner et al. | 428/152 |
| 5,804,011 A | 9/1998 | Dutta et al. | 156/160 |
| 5,804,021 A | 9/1998 | Abuto et al. | 156/252 |
| 5,804,286 A | 9/1998 | Quantrille et al. | 428/198 |
| 5,807,292 A | 9/1998 | Delmore | 602/8 |
| 5,807,368 A * | 9/1998 | Helmer | 604/373 |
| 5,814,178 A | 9/1998 | Jacobs | 156/290 |
| 5,824,004 A | 10/1998 | Osborn, III et al. | 604/385.2 |
| 5,837,352 A | 11/1998 | English et al. | 428/198 |
| 5,840,412 A | 11/1998 | Wood et al. | 428/284 |
| 5,843,057 A | 12/1998 | McCormack | 604/367 |
| 5,843,068 A * | 12/1998 | Allen et al. | 604/385.2 |
| 5,846,232 A | 12/1998 | Serbiak et al. | 604/385.2 |
| 5,851,935 A | 12/1998 | Srinivasan et al. | 442/328 |
| 5,853,881 A | 12/1998 | Estey et al. | 428/373 |
| 5,861,074 A | 1/1999 | Wu | 156/229 |
| 6,075,179 A * | 6/2000 | McCormack et al. | 604/367 |
| 6,140,442 A * | 10/2000 | Knight et al. | 526/348.1 |
| 6,177,607 B1 * | 1/2001 | Blaney et al. | 604/378 |
| 6,245,401 B1 * | 6/2001 | Ying et al. | 428/58 |

\* cited by examiner

EFFICIENT ZONED ELASTIC LAMINATE

FIELD OF THE INVENTION

This invention is directed to an elastic laminate material having an elastomeric element comprising at least two different elastomeric materials in series. In one embodiment, this invention is directed to an elastomeric element comprised of a high performance elastomer, for example LYCRA® polyurethane, and a lower performance elastomer, for example a metallocene-catalyzed polymer, in series. The elastomeric element exhibits high performance elastic properties at reduced material costs. In another embodiment, this invention is directed to a garment utilizing the elastomeric element to provide improved comfort, fit and appearance of the product.

BACKGROUND OF THE INVENTION

Elastic laminates are useful in many personal care products including diapers and undergarments. High performance elastomers, such as Lycra® spandex, are particularly useful because the laminates produced using these elastomers provide good product fit over an extended use period. However, such high performance elastomers are expensive. Further, the Lycra® polyurethane type laminates may provide a feminine or ruffled appearance that does not provide a flat or smooth surface that is discreet and invisible underneath clothing. Lower performance elastomers, including metallocene-catalyzed olefin polymers, have also been useful because of their low cost and clothlike appearance. Unfortunately, these less expensive elastomers do not necessarily provide high performance elastic properties and the thermoplastic laminates produced with these elastomers do not typically provide a good fit over an extended use period. As a result, products using these elastomers exhibit waist sag and poor leg fit. Generally, there is a need for an elastic laminate for personal care products that provides high performance elastic properties at a low material cost.

Related art alters or modifies the decitex, elongation or strand spacing of elastic elements in order to vary the tension across elasticized regions. In the present invention, the elastic properties of different elastomers are utilized to provide an elastic band that can be "tuned" to any particular area of a given product. This invention combines the high performance elastic properties of more expensive elastomers, such as Lycra® polyurethane, with the less expensive, lower performance elastomers, such as metallocene-catalyzed olefin polymers, to provide a material with high performance elastic properties and improved comfort, fit and appearance at a reduced material cost.

SUMMARY OF THE INVENTION

The present invention is directed to a multi-segment elastomeric band and laminate material useful in personal care products. The elastic band comprises at least two elastomeric segments adjacent to each other and in series. These segments have different polymer construction with different chemistries, molecular weight distributions, densities, and/or geometries. The elastomeric materials of the band can be defined so that a high performance elastomer, for example LYCRA® polyurethane, is used sparingly in regions where needed and the remaining regions of the band can comprise a lower performance elastomer, for example a single-site or metallocene-catalyzed olefin polymer. As a result, an elastomeric band is produced having high performance elastic properties where needed, at a reduced material cost. In another preferred embodiment, an elastic band is provided in which a first elastomeric material is comprised of a single-site or metallocene-catalyzed polymer having a density less than about 0.89 g/cc, and a second elastomeric material adjacent to the first, is comprised of another elastomeric polymer.

The elastic band may be bonded to one or two nonwoven webs, preferably spunbonded, to provide a multi-segment elastic laminate material. The elastomeric materials may be in the form of an elastomeric nonwoven web, for example, a spunbonded web, a meltblown web, a bonded carded web, or a combination thereof; a filament array; a film or a foam; or a laminate including one or more of the foregoing. The elastomeric materials may be permeable or impermeable to moisture vapor and/or liquid water, or have specific permeabilities.

Elastic polymers suitable for preparing the elastomeric band include, without limitation, elastomers made from block copolymers such as polyurethanes, copolyetheresters, polyamide polyether block copolymers, ethylene vinyl acetates (EVA) and the like; including polyurethanes available from E.I. Du Pont de Nemours Co., under the trade name LYCRA® (also known as "spandex"); elastomeric styrene-butadiene copolymers including those known as KRATON® materials which are available from Shell Chemical Company of Houston, Tex.; tetrablock copolymers, including styrene-poly(ethylene-propylene) elastomeric block copolymers available from the Shell Chemical Company of Houston, Tex. under the trade designation KRATON®; polyamides, including polyether block amides available from Ato Chemical Company, under the trade name PEBAX®; polyesters, such as those available from E.I. Du Pont de Nemours Co., under the trade name HYTREL®; single-site or metallocene-catalyzed polymers, including single-site or metallocene-catalyzed polyolefins having a density less than about 0.89 grams/cc available from Dow Chemical Co. under the trade name AFFINITY®; and natural and synthetic rubbers.

The adjacent elastomeric materials may be connected with a layer of adhesive, or by another bonding process known in the art, such as thermal bonding, ultrasonic bonding, chemical crosslinking, and mechanical lamination. The adjacent materials may be bonded together at edges which overlap each other. The elastomeric band can be elongated and bonded to an upper sheet and/or a lower sheet using any of the foregoing bonding technologies, to form the multi-segment elastic laminate. The resulting laminate exhibits hybrid properties of the adjacent elastomeric materials.

With the foregoing in mind, it is a feature and advantage of this invention to provide an elastomeric band and an elastic laminate material having high performance elastic properties and a more clothlike appearance while reducing material cost.

It is also a feature and advantage of this invention to provide a garment with improved fit, comfort and appearance having an elastomeric band comprising at least two different elastomeric materials adjacent to each other.

The foregoing and other features and advantages of the invention will become further apparent from the following detailed description of the preferred embodiments, read in conjunction with the drawings.

DEFINITIONS

Figure 1:
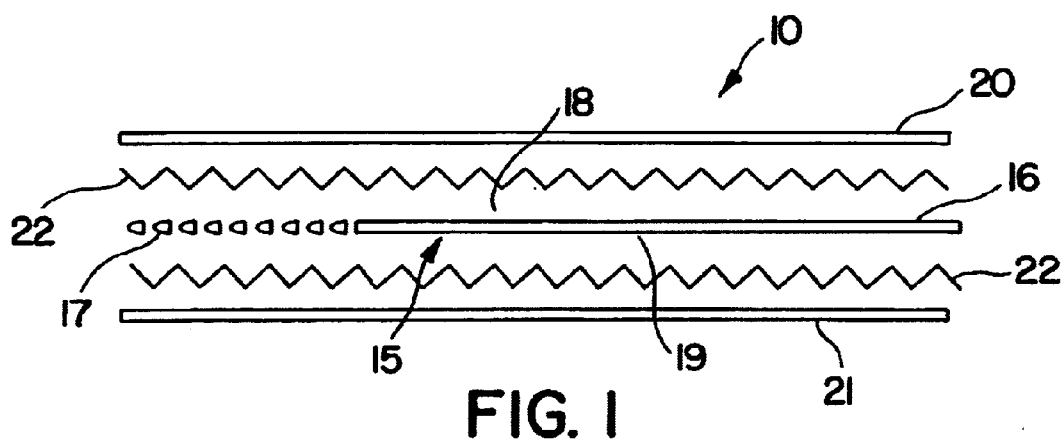
FIG. 1 is a side view of an exemplary dual elastic laminate material comprising an elastomeric band bonded to an upper sheet and a lower sheet. The elastic band includes two elastic materials in series with each other.

The terms "elastic" and "elastomeric" and "elastic properties" are used interchangeably herein to mean any material which, upon application of a biasing force, is stretchable to a stretched, biased length which is at least about 125 percent, that is about one and one quarter, of its relaxed, unbiased length, and which will recover at least 40 percent of its elongation upon release of the stretching, elongating force. A hypothetical example which will satisfy this definition of an elastomeric material would be a one (1) inch sample of a material which is elongatable to at least 1.25 inches and which, upon being elongated to 1.25 inches and released, will recover to a length of not more than 1.15 inches. Many elastic materials may be stretched to much more than 125 percent of their relaxed length (suitably, to at least 150 percent of their relaxed length), and many of these will recover to substantially their original relaxed length upon release of the stretching, elongating force and this latter class of materials is generally preferred for purposes of the present invention.

As used herein, the term "nonelastic" refers to any material which does not fall within the definition of "elastic," above.

As used herein, the term "in series" means any two elastic materials that are laterally adjacent with each other, including materials whose edges touch, but do not overlap; materials whose edges overlap each other, but which otherwise do not overlap; and materials spaced at a distance in the same plane.

As used herein, the term "nonwoven web" means a web that has a structure of individual fibers or threads which are interlaid, but not in an identifiable, repeating manner. Nonwoven webs have been, in the past, formed by a variety of processes such as, for example, melt-blowing processes, spunbonding processes and bonded carded web processes.

As used herein, the term "microfibers" means small diameter fibers having an average diameter not greater than about 100 microns, for example, having a diameter of from about 0.5 microns to about 50 microns, more particularly, microfibers may have an average diameter of from about 4 microns to about 40 microns.

As used herein, the term "meltblown fibers" means fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al., the disclosure of which is hereby incorporated by reference.

As used herein, the term "spunbonded fibers" refers to small diameter fibers which are formed by extruding a molten thermoplastic material as filaments from a plurality of fine, usually circular, capillaries of a spinnerette with the diameter of the extruded filaments then being rapidly reduced as by, for example, eductive drawing or other well-known spunbonding mechanisms. The production of spunbonded nonwoven webs is illustrated in patents such as, for example, in U.S. Pat. No. 4,340,563 to Appel et al.; U.S. Pat. No. 3,692,618 to Dorschner et al. and U.S. Pat. No. 3,802,817 to Matsuki et al. The disclosures of these patents are hereby incorporated by reference.

As used herein, the term "film" refers to polymeric sheets formed using a blown film or cast film extrusion process, or another film extrusion process, and does not include nonwoven webs as defined above.

Unless specifically set forth and defined or otherwise limited, the terms "polymer" or "polymer resin" as used herein generally include, but are not limited to, homopolymers, copolymers, such as, for example, block, graft, random and alternating copolymers, terpolymers, etc. and blends and modifications thereof Further, unless otherwise specifically limited, the terms "polymer" or "polymer resin" shall include all possible geometrical configurations of the material. These configurations include, but are not limited to, isotactic, syndiotactic and random symmetries.

As used herein, the terms "single-site catalyzed polymer" and "metallocene-catalyzed polymer" refer to a polymer having a particular range of stretch and recovery characteristics produced by the single-site (e.g. metallocene-catalyzed) process. These polymers have the unique advantage of having a very narrow molecular range. Polydispersity numbers (Mw/Mn) of below 4 and even below 2 are possible for single-site catalyzed polymers. These polymers have a controlled short chain branching distribution when compared to otherwise similar non-single site catalyzed polymers.

As used herein, the term "hysteresis" is a measure of how well an elastic material retains its elastic properties over a number of stretches. The loss of the hysteresis over a number of stretch cycles should desirably be minimal. For example, a material having no hysteresis loss will show the same force measured at 30 percent elongation during the retraction in the second cycle as the force of extension at 30 percent elongation during the first cycle. Dividing the first cycle force of extension by the second cycle force of retraction shows that such a material will have a hysteresis of 1.0.

The term "polydispersity number" or "polydispersity index" is defined as weight average molecular weight divided by the number average molecular weight (Mw/Mn). Elastomers with a very low or narrow polydispersity number, e.g. 4 or less, are blended with a base polymer to produce metallocene-catalyzed polymers.

As used herein the term "garment" means any type of apparel which may be worn. This includes industrial workwear like coveralls, undergarments, pants, shirts, jackets, gloves, socks, and the like, as well as medical protective garments.

As used herein the term "personal care product" means diapers, training pants, absorbent underpants, adult incontinence products, and feminine hygiene products.

DETAILED DESCRIPTION OF THE PREFERRED EMBODIMENTS

FIG. 1 shows a side view of an exemplary dual elastic laminate material 10. Dual elastic laminate material 10 comprises an elastomeric band 15 comprised of at least one first elastomeric segment 16 and at least one second elastomeric segment 17 in series. The first elastomeric segment 16 and the second elastomeric segment 17 are comprised of polymers of different polymeric construction, i.e. different chemistries, molecular weight distributions, densities, and/or geometries. Therefore, elastomeric segments 16, 17 may have elastic properties substantially different from one another. In one embodiment, one elastomeric segment 16 or 17 may be stretchable to at least 200% of its initial relaxed length while the other elastomeric segment 17 or 16 may be stretchable only to 125% to less than about 200% of its initial relaxed length. In one embodiment, elastomeric segment 16 comprises a single-site (e.g. metallocene) catalyzed olefin polymer having a density less than about 0.89 grams/cc, and elastomeric segment 17 comprises a LYCRA® polyurethene. In another embodiment, elastomeric segment 16 comprises a single-site catalyzed polymer and elastomeric segment 17 comprises another, Ziegler-Natta polymer.

Elastic segments 16, 17 may each be an elastomeric nonwoven web, for example, a spunbonded web, a meltblown web, a bonded carded web, or a combination thereof. If the segment is a web of meltblown fibers, it may include meltblown microfibers. The elastic nonwoven webs may be formed using conventional processes, including the spunbond and meltblowing processes described in the above "DEFINITIONS." Elastomeric segments 16, 17 may also be filament arrays, films, foams and ribbons, produced by conventional extrusion processes.

Suitable elastic polymers for producing elastomeric segments 16, 17 include, without limitation, elastomers made from block copolymers such as polyurethanes, copolyetheresters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly (styrene/ethylene-butylene/styrene) and the like. Examples of suitable polyurethanes include those available from E.I. Du Pont de Nemours Co., under the trade name LYCRA® polyurethane.

Suitable elastomeric resins include block copolymers having general formula A-B-A' or A-B, where A and A' are each a thermoplastic polymer end block which contains a styrenic moiety such as a poly (vinyl arene) and where B is an elastomeric polymer midblock such as a conjugated diene or a lower alkene polymer. Block copolymers of the A-B-A' type can have different or the same thermoplastic block copolymers for the A and A' blocks, and the present block copolymers are intended to embrace linear, branched and radial block copolymers. Examples of such elastomeric copolymers include those known as KRATON® materials which are available from Shell Chemical Company of Houston, Tex. An elastomeric nonwoven web may be formed from, for example, elastomeric (polystyrene/poly (ethylene-butylene)/polystyrene) block copolymers available from the Shell Chemical Company of Houston, Tex. under the trade name KRATON® G. KRATON® block copolymers are available in several different formulations, a number of which are identified in U.S. Pat. Nos. 4,663,220 and 5,304,599, hereby incorporated by reference.

Polymers composed of an elastomeric A-B-A-B tetrablock copolymer may also be used in the practice of this invention. Such polymers are discussed in U.S. Pat. No. 5,332,613 to Taylor et al. In such polymers, A is a thermoplastic polymer block and B is an isoprene monomer unit hydrogenated to substantially a poly(ethylene-propylene) monomer unit. An example of such a tetrablock copolymer is a styrene-poly(ethylene-propylene)-styrene-poly (ethylene-propylene) or SEPSEP elastomeric block copolymer available from the Shell Chemical Company of Houston, Tex. under the trade designation KRATON®.

Other suitable materials include polyamide elastomeric materials, including polyether block amides available from Ato Chemical Company, under the trade name PEBAX®; polyester elastomeric materials, such as those available from E.I. Du Pont de Nemours Co., under the trade name HYTREL®; single-site or metallocene-catalyzed polyolefins having a density less than about 0.89 grams/cc, available from Dow Chemical Co. under the trade name AFFINITY®; and natural and synthetic rubbers.

Processing aids may be added to the elastomeric polymers to assist in producing films and meltblown fibers from these elastomers. For example, a polyolefin processing aid may be blended with the elastomeric polymer to improve the processability of the composition. Useful blending polyolefin materials include polyethylene, polypropylene, and polybutene, including ethylene copolymers, propylene copolymers and butene copolymers. However, these processing aids have a negative effect on the hysteresis of the base elastomer. Hysteresis is a measure of how well an elastic material retains its elastic properties over a number of stretch cycles.

The processability of the elastomers can be improved by adding a metallocene polyolefin, without negatively affecting the hysteresis of the base polymer. Such polymers have a very low or narrow polydispersity number, e.g. Mw/Mn of 4 or less, and may be made by a process referred to as the metallocene polymerization process. As taught in U.S. Pat. No. 5,853,881 issued to Estey, et al., the description of which is incorporated herein by reference, the single-site process generally uses a metallocene catalyst which is activated, i.e. ionized, by a co-catalyst. Single-site catalyzed polymers have the unique advantage of having a very narrow molecular range. Polydispersity numbers (Mw/Mn) of below 4 and even below 2 are possible for metallocene produced polymers. These polymers also have a controlled short chain branching distribution when compared to otherwise similar Ziegler-Natta produced polymers.

The single-site catalysts are generally referred to as "single site" or "metallocene" catalysts to distinguish them from the conventional Ziegler-Natta catalysts which have multiple reaction sites. Single-site catalyzed polymers have a particular range of stretch and recovery characteristics.

The strategic and efficient use of high performance elastic materials, such as LYCRA® spandex (polyurethane), in critical areas with lower performance elastomers in the remaining areas of dual elastic laminate material 10 results in a laminate material 10 having high performance elastic properties where needed, at a reduced overall material cost. The material has improved comfort, fit and enhanced appearance. Referring again to FIG. 1, elastic segments 16 and 17 may be combined by positioning them adjacent each other as shown, and preferably joining them together at their edges. The adjacent edges of segments 16 and 17 may slightly overlap each other to facilitate bonding. Bonding may be accomplished using processes known in the art, including adhesive bonding, thermal bonding, ultrasonic bonding, chemical crosslinking between the layers, ultrasonic bonding, mechanical stitching, and the like.

After elastomeric segment 16 is preferably bonded to elastomeric segment 17 to form combined elastomeric band 15, laminate material 10 is formed by elongating elastomeric band 15 and bonding elastomeric band 15 on a first side 18 to an upper sheet 20 and on a second side 19 to a lower sheet 21. This bonding may be accomplished via adhesive layers 22 between the elastic band 15 and the sheets 20 and 21. Layers 22 may comprise a meltblown adhesive, for instance. Other bonding means known in the art may be utilized to bond elastomeric band 15 to upper sheet 20 and lower sheet 21 including thermal bonding, ultrasonic bonding, mechanical stitching, and the like. Upper sheet 20 and lower sheet 21 may each be a nonwoven web, for example, a spunbonded web, a meltblown web, a bonded carded web or a combination thereof Upper sheet 20 and lower sheet 21 may also each be a filament array, a film or a foam.

Figure 2:
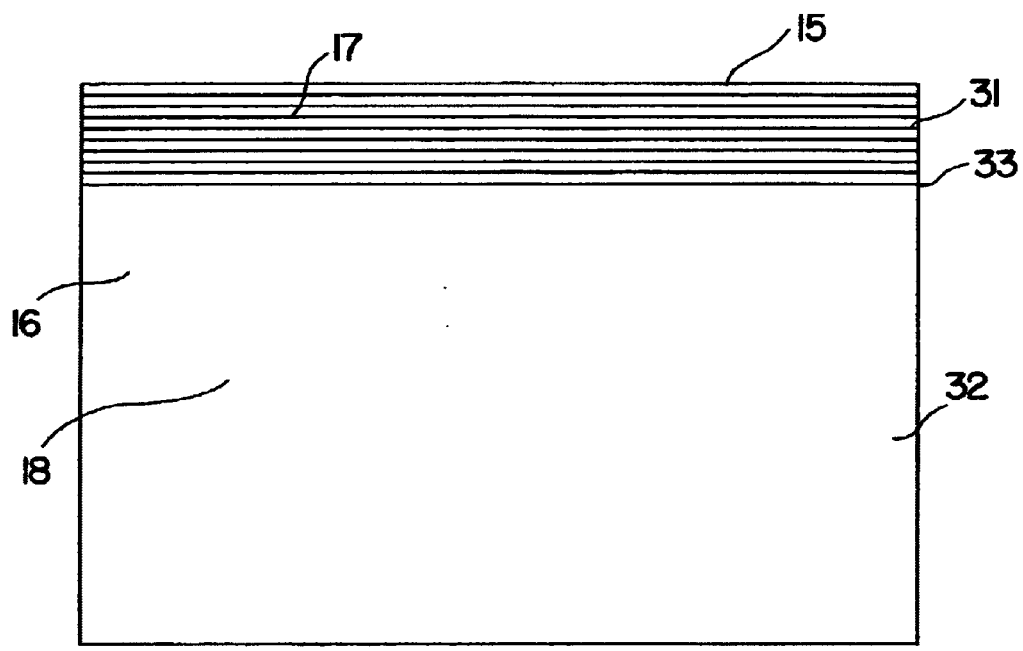
FIG. 2 is a top view of the exemplary elastomeric band of FIG. 1 (with upper sheet removed) comprising a first elastomeric material connected in series to a second different elastomeric material.

FIG. 2 shows a top view of elastomeric band 15, with the layers 20 and 22 removed. Elastomeric band 15 comprises a first elastomeric material 16 and a second elastomeric material 17. In one embodiment, first elastomeric material 16 comprises a metallocene-catalyzed olefin polymer (i.e. polyethylene) film 32 and second elastomeric material 17 comprises a LYCRA® polyurethane having a plurality of spandex strands 31. Spandex strands 31 and metallocene-catalyzed polymer film 32 can be attached with a layer of 5 gsm meltblown adhesive along interface 33. Spandex strands 31 and film 32 can also be attached by alternative bonding processes well known in the art, as described above. In an alternative embodiment, film 32 may be replaced with a ribbon or nonwoven web of similar polymer construction.

In another embodiment, first elastomeric segment 16 may be composed of a first polymer from the above list, and second elastomeric segment 17 may be composed of a second polymer from the above list. Alternatively, first and second elastic segments 16 and 17 in series may be different material types, such as film and nonwoven web, or one type of nonwoven web (e.g. spunbond) versus another type of nonwoven web (e.g. meltblown). Alternatively, first and second segments 16 and 17 in series may have different thickness, shapes, molecular weights, or may differ in more than one of the foregoing respects. The combined elastomeric band 15 will exhibit hybrid properties of the two segments 16 and 17, often providing the desired properties of the higher cost material where needed, and utilizing the lower cost material where the properties of the higher cost material are not needed.

The hybrid elastic band 15 can be employed in a wide variety of disposable absorbent products including, for instance, diapers, training pants, swim wear, absorbent underpants, adult incontinence products, feminine hygiene products, and medical absorbent garments. The hybrid elastic band is especially useful in absorbent articles requiring elastic in the waist and/or leg regions of a wearer.

Figure 3:
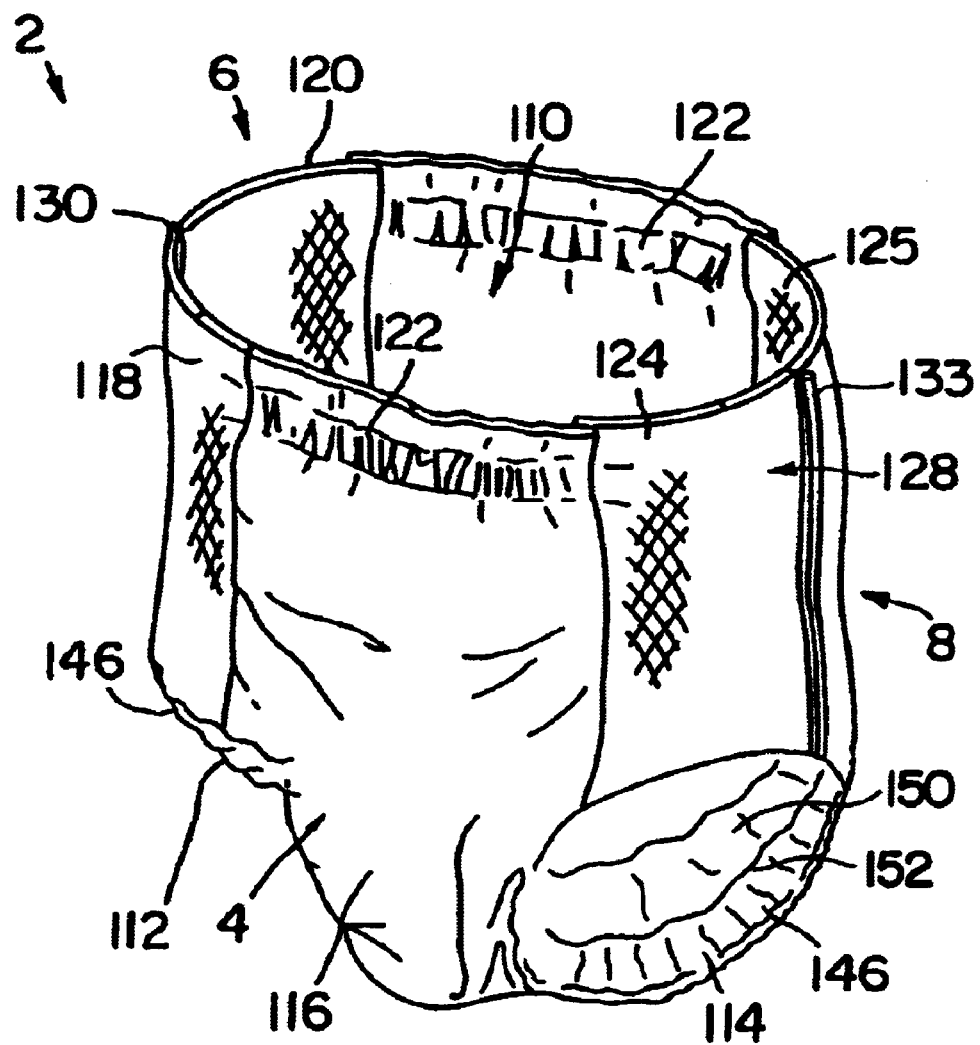
FIG. 3 is a perspective view of an exemplary pant-like absorbent garment having elastic bands in the waist elastic regions and the leg elastic regions of the pant-like absorbent garment.

Disposable absorbent garments having a pant-like configuration are used for child training pants, adult incontinence garments, diapers, swimsuits and the like. Referring to FIG. 3, a pant-like absorbent garment 2 includes a waste containment section 4 and two side portions 6 and 8 defining a waist opening 110 and a pair of leg openings 112 and 114. The side panel 6 includes stretchable panels 118 and 120 joined together at seam 130. The side panel 8 includes stretchable panels 124 and 126 joined together at seam 133. Seams 130 and 133 extend longitudinally from the waist opening 110 to the leg openings 112 and 114 of the garment 2.

The waist containment section 4 includes multiple layers (not shown) including, for instance, a liquid-permeable inner layer, an absorbent core layer, and a liquid-permeable outer cover layer 116 which faces away from the wearer. The waste containment section 4 also includes elasticized waist portions 122 on the front and back of the garment. The leg opening portion 112 and 114 also include elastic portions 146 which extend substantially around the portion of the leg openings defined by the waste containment section 4.

The disposable garment also includes leak guards in both leg openings, which help prevent lateral leakage of waste material through the leg openings. The leak guards have commonly been provided by elasticized flap portions 150 which are connected to the interior of the garment along the lower part of each leg opening. During use, the elasticized flap portions 150 fit snugly against the wearer and effectively block most spillage of waste material from the leg openings.

The hybrid elastic bands 15 of the invention can be used, for instance, in the waist elastic regions 122 and/or the leg elastic regions 146 of the pant-like absorbent garment 2. The elastic segments 16 and 17 can be selected and provided in any ratio to provide an optimum combination of high performance and low cost. Elastic bands 15 can be attached to garment 2 using a variety of known techniques including adhesive bonding, ultrasonic bonding, thermal bonding, stitch bonding, and the like. If desired, the elastic bands 15 may be provided in the form of the laminate 10 described above.

It is to be understood that variations and modifications of the present invention may be made without departing from the scope of the present invention. It is also to be understood that the scope of the present invention is not to be interpreted as limited to the specific embodiments disclosed herein. The scope of the invention is indicated in the appended claims, and all changes that fall within the meaning and range of equivalents are intended to be embraced therein.

I claim:

1. A garment having one or more openings at least partially surrounded by an elastomeric band,
   the elastomeric band comprising a first elastomeric segment and a second elastomeric segment in series,
   the first and second elastomeric segments being of different polymer compositions;
   at least one of the elastomeric segments comprising a plurality of spaced apart elastic elements.

2. The garment of claim 1, wherein the first and second elastomeric segments each have a relaxed length;
   the first elastomeric segment being stretchable to at least 200% of its relaxed length;
   the second elastomeric segment being stretchable to between 125% and less than 200% of its relaxed length.

3. The garment of claim 1, wherein one of the first and second elastomeric segments comprises a film, and the other of the first and second elastomeric segments comprises a nonwoven web.

4. The garment of claim 1, wherein each of the first and second elastomeric segments comprises a different polymer selected from the group consisting of polyurethanes, copolyetheresters, polyamide polyether block copolymers, styrene-ethylene-butylene copolymers, styrene-ethylene-propylene copolymers, vinyl arene copolymers, metallocene-catalyzed olefin polymers, isoprene polymers, and combinations thereof.

5. The garment of claim 1, wherein the first elastomeric segment comprises polyurethane.

6. The garment of claim 5, wherein the second elastomeric segment comprises an elastomeric olefin polymer having a density not greater than 0.89 grams/cc.

7. The garment of claim 1, wherein the first elastomeric segment comprises an isoprene polymer.

8. The garment of claim 7, wherein the second elastomeric segment comprises an elastomeric olefin polymer having a density greater than 0.89 grams/cc.

9. The garment of claim 1, wherein the first elastomeric segment comprises a styrene-butadiene copolymer.

10. The garment of claim 9, wherein the second elastomeric segment comprises an elastomeric olefin polymer having a density not greater than 0.89 grams/cc.

11. The garment of claim 4, wherein one of the first and second elastomeric segments comprises a single-site catalyzed olefin polymer.

12. The garment of claim 1, wherein the first elastomeric segment and the second elastomeric segment are connected by an adhesive.

13. The garment of claim 1, wherein the first elastomeric segment and the second elastomeric segment are connected by thermal bonding.

14. The garment of claim 1, wherein the first elastomeric segment and the second elastomeric segment are connected by ultrasonic bonding.

15. The garment of claim 1, wherein the first elastomeric segment and the second elastomeric segment are connected by chemical crosslinking.

16. The garment of claim 1, wherein the first elastomeric segment and the second elastomeric segment are connected by mechanical stitching.

17. The garment of claim 1, wherein one of the elastomeric segments comprises a polyolefin film prepared from a single-site catalyzed olefin polymer having a density not greater than 0.89 grams/cc.

18. A garment comprising an elastic laminate material, the elastic laminate material comprising:

an elastomeric band comprising at least one first elastomeric segment in series with at least one second elastomeric segment, the first elastomeric segment and the second elastomeric segment comprising different elastomeric polymers at least one of the elastomeric segments comprising a plurality of spaced apart elastic elements;

an upper sheet bonded to a first side of the elastomeric band; and a lower sheet bonded to a second side of the elastomeric band.

19. A disposable garment including at least one elastic band, the elastic band comprising:

at least one first elastomeric segment; and at least one second elastomeric segment connected in series with the first elastomeric segment;

the first elastomeric segment and the second elastomeric segment comprising different elastomeric polymers;

at least one of the elastomeric segments comprising a plurality of spaced apart elastic elements.

20. The disposable garment of claim 19, comprising a diaper.

21. The disposable garment of claim 19, comprising training pants.

22. The disposable garment of claim 19, comprising swim wear.

23. The disposable garment of claim 19, comprising absorbent underpants.

24. The disposable garment of claim 19, comprising an adult incontinence garment.

25. The disposable garment of claim 19, comprising a feminine hygiene product.

26. The disposable garment of claim 19, comprising a medical garment.

* * * * *